United States Patent
Biedermann et al.

(10) Patent No.: US 11,154,334 B2
(45) Date of Patent: *Oct. 26, 2021

(54) POLYAXIAL BONE ANCHORING DEVICE WITH ENLARGED PIVOT ANGLE

(71) Applicant: BIEDERMANN TECHNOLOGIES GMBH & CO. KG, Donaueschingen (DE)

(72) Inventors: Lutz Biedermann, VS-Villingen (DE); Wilfried Matthis, Weisweil (DE)

(73) Assignee: BIEDERMANN TECHNOLOGIES GMBH & CO. KG, Donaueschingen (DE)

(*) Notice: Subject to any disclaimer, the term of this patent is extended or adjusted under 35 U.S.C. 154(b) by 0 days.

This patent is subject to a terminal disclaimer.

(21) Appl. No.: 16/924,897

(22) Filed: Jul. 9, 2020

(65) Prior Publication Data

US 2020/0405354 A1    Dec. 31, 2020

Related U.S. Application Data

(63) Continuation of application No. 16/107,387, filed on Aug. 21, 2018, now Pat. No. 10,722,272, which is a (Continued)

(30) Foreign Application Priority Data

Jul. 27, 2012 (EP) .................... 12178289

(51) Int. Cl.
*A61B 17/70* (2006.01)
*A61B 17/86* (2006.01)

(52) U.S. Cl.
CPC ...... *A61B 17/7037* (2013.01); *A61B 17/7032* (2013.01); *A61B 17/7035* (2013.01); *A61B 17/7038* (2013.01); *A61B 17/8605* (2013.01)

(58) Field of Classification Search
CPC ............ A61B 17/7032; A61B 17/7038; A61B 17/7037
See application file for complete search history.

(56) References Cited

U.S. PATENT DOCUMENTS 5,429,639 A    7/1995 Judet
5,584,834 A    12/1996 Errico
(Continued)

FOREIGN PATENT DOCUMENTS

EP    2 022 423 A1    2/2009
JP    2010-533556 A    10/2010
(Continued)

OTHER PUBLICATIONS

Extended European Search Report for European Application No. 12178289.0, European Search Report dated Nov. 20, 2012 and dated Dec. 6, 2012 (7 pgs.).

*Primary Examiner* — Christina A Sevilla
(74) *Attorney, Agent, or Firm* — Lewis Roca Rothgerber Christie LLP

(57) ABSTRACT

A bone anchoring device includes a bone anchoring element with a spherical segment-shaped head, a receiving part configured to couple a rod to the bone anchoring element, and having a top end, a bottom end, a first passage at the bottom end with a first longitudinal axis, and a second passage at the top end with a second longitudinal axis that intersects the first longitudinal axis, a compression element, and a locking element. The receiving part also has a recess for the rod, the recess extending from the top end towards the bottom end and having a bottom that extends along an axis that is perpendicular to the second longitudinal axis. The receiving part or the compression element further has a seat. The compression element is configured to move along (Continued)

the first longitudinal axis while the locking element is configured to move along the second longitudinal axis.

24 Claims, 11 Drawing Sheets

Related U.S. Application Data continuation of application No. 15/008,273, filed on Jan. 27, 2016, now Pat. No. 10,064,659, which is a continuation of application No. 13/948,700, filed on Jul. 23, 2013, now Pat. No. 9,277,942.

(60) Provisional application No. 61/676,485, filed on Jul. 27, 2012.

(56) References Cited

U.S. PATENT DOCUMENTS

| | | | |
|---|---|---|---|
| 5,797,911 A | 8/1998 | Sherman | |
| 5,882,350 A | 3/1999 | Ralph | |
| 6,280,442 B1 | 8/2001 | Barker | |
| 6,736,820 B2 | 5/2004 | Biedermann | |
| 6,974,460 B2 | 12/2005 | Carbone | |
| 7,081,116 B1 | 7/2006 | Carly | |
| 9,277,942 B2 | 3/2016 | Biedermann et al. | |
| 9,717,534 B2* | 8/2017 | Jackson | A61B 17/7037 |
| 2002/0091386 A1 | 7/2002 | Martin | |
| 2003/0055426 A1* | 3/2003 | Carbone | A61B 17/7034 |
| | | | 606/271 |
| 2003/0187433 A1* | 10/2003 | Lin | A61B 17/7032 |
| | | | 606/278 |
| 2004/0102781 A1 | 5/2004 | Jeon | |
| 2005/0038430 A1 | 2/2005 | McKinley | |
| 2005/0080415 A1 | 4/2005 | Keyer | |
| 2005/0154393 A1* | 7/2005 | Doherty | A61B 17/7037 |
| | | | 606/272 |
| 2005/0187548 A1* | 8/2005 | Butler | A61B 17/7038 |
| | | | 606/278 |
| 2005/0277919 A1* | 12/2005 | Slivka | A61B 17/7032 |
| | | | 606/256 |
| 2006/0229615 A1 | 10/2006 | Abdou | |
| 2006/0264933 A1 | 11/2006 | Baker | |
| 2006/0276789 A1* | 12/2006 | Jackson | A61B 17/7037 |
| | | | 606/916 |
| 2006/0293659 A1 | 12/2006 | Alvarez | |
| 2007/0265621 A1 | 11/2007 | Matthis | |
| 2008/0161859 A1 | 7/2008 | Nilsson | |
| 2008/0177322 A1 | 7/2008 | Davis | |
| 2008/0234823 A1* | 9/2008 | Landry | A61B 17/7037 |
| | | | 623/17.16 |
| 2008/0306513 A1* | 12/2008 | Winslow | A61P 11/06 |
| | | | 606/246 |
| 2009/0076550 A1* | 3/2009 | Bernhardt, Jr. | A61B 17/7037 |
| | | | 606/246 |
| 2009/0088809 A1* | 4/2009 | Fisher | A61B 17/8605 |
| | | | 606/302 |
| 2010/0036436 A1* | 2/2010 | Winslow | A61B 17/7038 |
| | | | 606/305 |
| 2010/0087867 A1* | 4/2010 | Klein | A61B 17/7007 |
| | | | 606/278 |
| 2010/0168800 A1 | 7/2010 | Biedermann | |
| 2010/0298891 A1* | 11/2010 | Jackson | A61B 17/7008 |
| | | | 606/308 |
| 2011/0040338 A1 | 2/2011 | Jackson | |
| 2011/0276098 A1 | 11/2011 | Biedermann et al. | |
| 2012/0095512 A1* | 4/2012 | Nihalani | A61B 17/7037 |
| | | | 606/251 |
| 2012/0123477 A1 | 5/2012 | Landry | |
| 2012/0209335 A1* | 8/2012 | Termyna | A61B 17/7037 |
| | | | 606/300 |
| 2012/0303063 A1 | 11/2012 | Cahill | |
| 2013/0197585 A1* | 8/2013 | Jackson | A61B 17/8685 |
| | | | 606/278 |
| 2013/0218213 A1 | 8/2013 | Lemoine | |
| 2014/0031880 A1 | 1/2014 | Biedermann | |
| 2014/0142633 A1 | 5/2014 | Jackson | |
| 2019/0274734 A1* | 9/2019 | Jackson | A61B 17/7002 |
| 2020/0069341 A1* | 3/2020 | Abbasi | A61B 17/7037 |

FOREIGN PATENT DOCUMENTS

| | | |
|---|---|---|
| WO | WO 2009/012247 A1 | 1/2009 |
| WO | WO 2012/048004 A2 | 4/2012 |
| WO | WO 2012/162550 A1 | 11/2012 |

\* cited by examiner

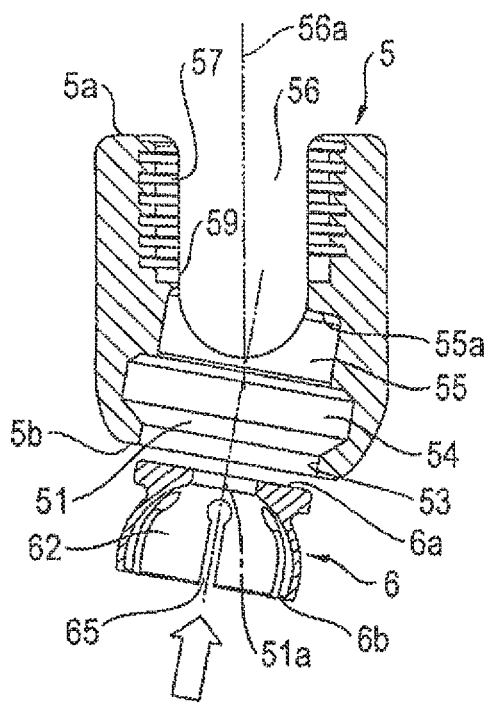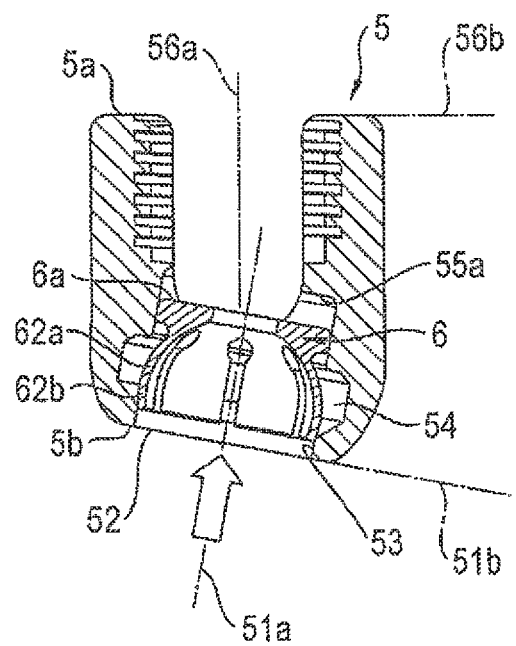
Fig. 11  Fig. 12
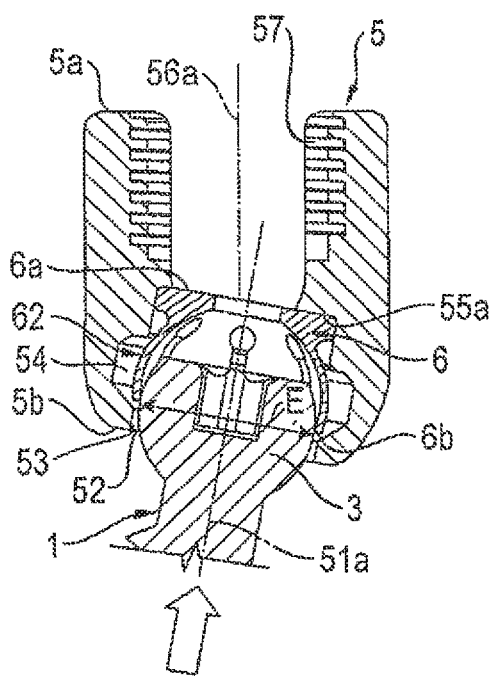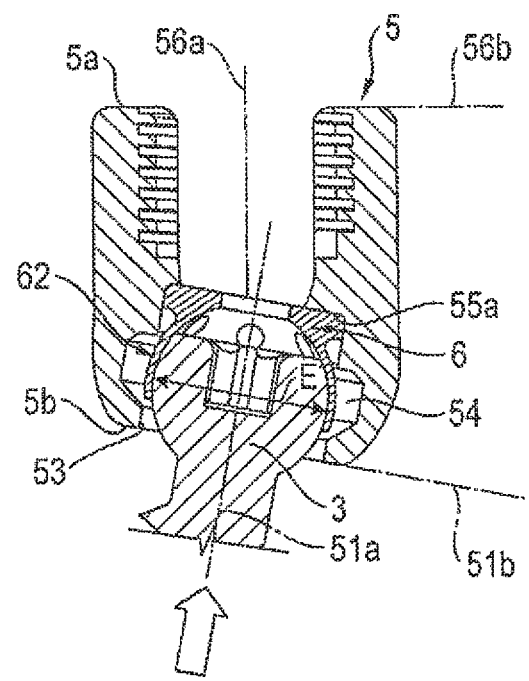
Fig. 13  Fig. 14

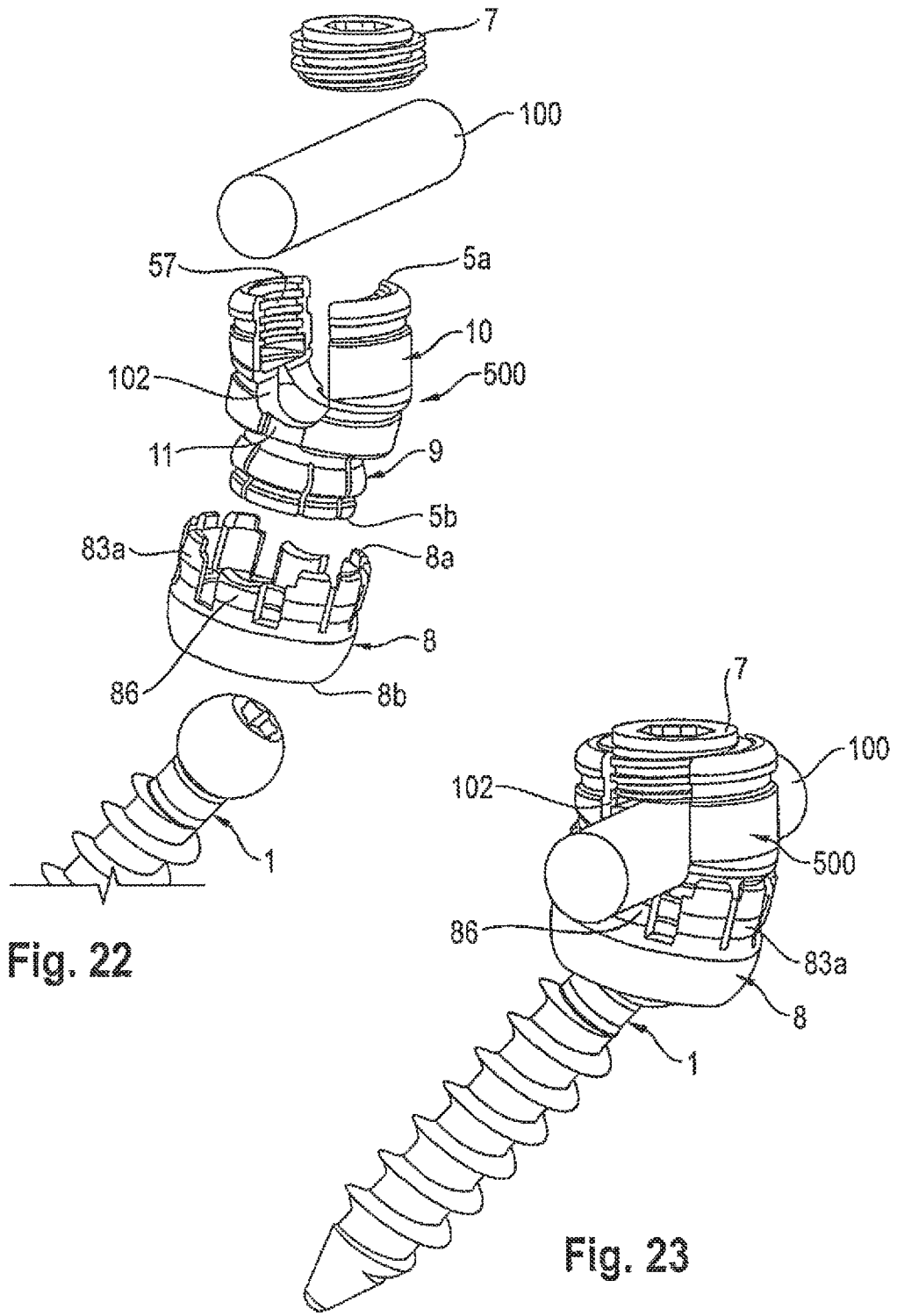

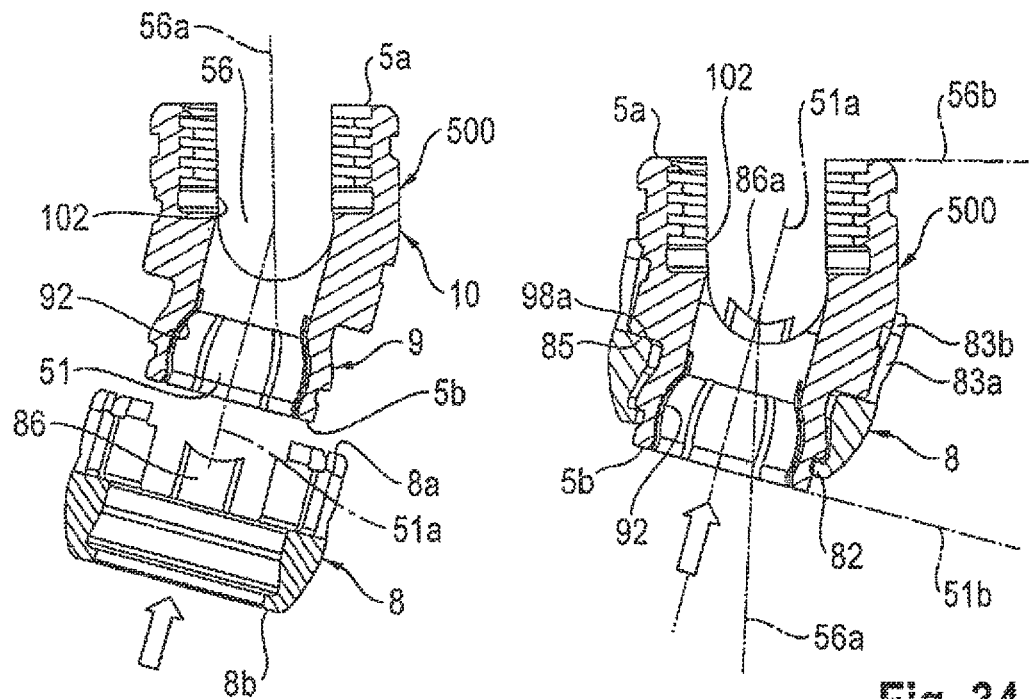
Fig. 33
Fig. 34
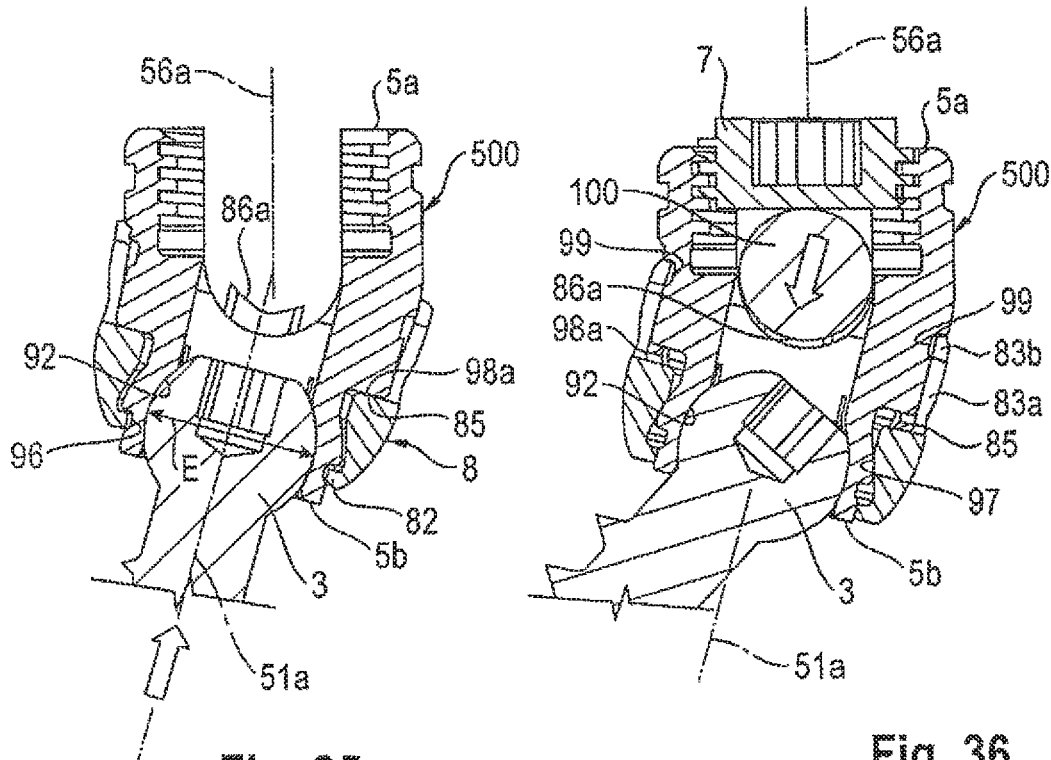
Fig. 35
Fig. 36

POLYAXIAL BONE ANCHORING DEVICE
WITH ENLARGED PIVOT ANGLE

CROSS-REFERENCE TO RELATED APPLICATION(S)

This application is a continuation of U.S. patent application Ser. No. 16/107,387, filed Aug. 21, 2018, which is a continuation of U.S. patent application Ser. No. 15/008,273, filed Jan. 27, 2016, now U.S. Pat. No. 10,064,659, which is a continuation of U.S. patent application Ser. No. 13/948,700, filed Jul. 23, 2013, now U.S. Pat. No. 9,277,942, which claims priority to and the benefit of U.S. Provisional Patent Application Ser. No. 61/676,485, filed Jul. 27, 2012, the contents of which are hereby incorporated by reference in their entirety, and claims priority from European Patent Application EP 12 178 289.0, filed Jul. 27, 2012, the contents of which are hereby incorporated by reference in their entirety.

BACKGROUND

Field of the Invention

The invention relates to a polyaxial bone anchoring device providing a pivot angle that is enlarged to one side compared to an opposite side. The polyaxial bone anchoring device comprises a bone anchoring element with a head and a shank and a receiving part for receiving a rod for coupling the rod to the bone anchoring element. The receiving part has two passages, each coaxial with a longitudinal axis, wherein the longitudinal axes of the two passages intersect one another and wherein one of the passages includes a seat configured to allow pivoting of the head. The head is insertable into the seat from a bottom end of the receiving part.

Description of Related Art

A polyaxial bone anchoring device with an enlarged pivot angle to one side is known from U.S. Pat. No. 6,736,820 B2. This bone anchoring device comprises a screw member that is pivotably held in a receiving part, wherein the receiving part has an open first bore and a second bore on the end opposite to the first bore. On the bottom of the first bore, a seat for the head is provided. In order that the screw member can be pivoted to at least one side by an enlarged angle, an edge bounding the free end of the second bore viewed relative to the axis of the first bore is of asymmetric construction. The diameter of the second bore is greater than that of a threaded section of the screw member and smaller than that of the head.

Another bone anchoring device with an enlarged pivot angle is known from U.S. Pat. No. 6,974,460 B2. It includes a coupling element having an inner surface defining a first bore coaxial with a first longitudinal axis, and a second bore coaxial with a second longitudinal axis, whereby the second longitudinal axis intersects the first longitudinal axis. The coupling element has a seat adjacent to the lower end of the coupling element for the head of a bone anchoring element.

The polyaxial bone anchoring devices described above are top-loading anchoring devices wherein the anchoring element is inserted into the receiving part from an upper end thereof.

A bottom-loading polyaxial bone anchoring device is known from US 2011/0276098 A1. This polyaxial anchoring device comprises a rod receiving portion and a head receiving portion and an outer locking ring that is configured to compress the head receiving portion to clamp and finally lock the head. The anchoring element is insertable into the receiving part from a bottom end of the receiving part.

SUMMARY

It is the object of the invention to provide a polyaxial bone anchoring device that provides for enlarged angulation and that provides for an increased variety of applications.

A polyaxial bone anchoring device according to embodiments of the invention is a bottom loading polyaxial bone anchoring device, wherein the anchoring element can be inserted into a receiving part from a bottom end of the receiving part. This allows for providing a modular system. In one embodiment, the bone anchoring device may be delivered by a manufacturer as a receiving part pre-assembled with an inner compression member, and separate therefrom, one or a plurality of different bone anchoring elements. In another embodiment, the bone anchoring device may be delivered by a manufacturer as a receiving part pre-assembled with an outer locking ring and also separate therefrom one or a plurality of bone anchoring elements. By means of this, various bone anchoring elements with shanks having different diameters, thread forms and/or various other different features can be combined with a receiving part according to actual clinical requirements in a particular clinical situation. This gives a surgeon or other practitioner a more diverse or wider choice of implants.

In addition, due to such modularity, the costs of stock-holding can be decreased.

The polyaxial bone anchoring device provides for an enlarged pivot angle to one side compared to an opposite side, i.e. has a favored angle design. A pull-out force that is necessary to pull out the bone anchoring element through an opening at the bottom end of the receiving part is comparable to or at least not less than a pull-out force of comparable polyaxial bone anchoring devices that do not have a favored angle design. This renders the bone anchoring device particularly suitable for applications of lateral mass fixation, for example, at the cervical spine.

The polyaxial bone anchoring device does not require additional parts compared to anchoring devices without a favored angle design. Hence, the polyaxial bone anchoring device provides for reduced dimensions in terms of height as well as in terms of diameter, which makes it particularly suitable for applications where small-sized anchoring devices are required, such as in the fields of cervical spine surgery or pediatric applications, trauma, and minimally open or minimally invasive applications for bone surgery.

BRIEF DESCRIPTION OF THE DRAWINGS

Further features and advantages will become apparent from the description of embodiments by means of accompanying drawings. In the drawings:

FIGS. 11 to 14 show cross-sectional views of steps of mounting the compression member and the bone anchoring element to the receiving part according to the first embodiment, the section taken along line A-A in FIG. 5.

FIG. 22 shows an exploded perspective view of a polyaxial bone anchoring device according to a second embodiment.

FIG. 23 shows a perspective view of the polyaxial bone anchoring device of FIG. 22 in an assembled state.

FIGS. 33 to 36 show cross-sectional views of steps of assembling the polyaxial bone anchoring device according to the second embodiment, the section taken along line C-C in FIG. 26.

DETAILED DESCRIPTION

Figures 1, 2:
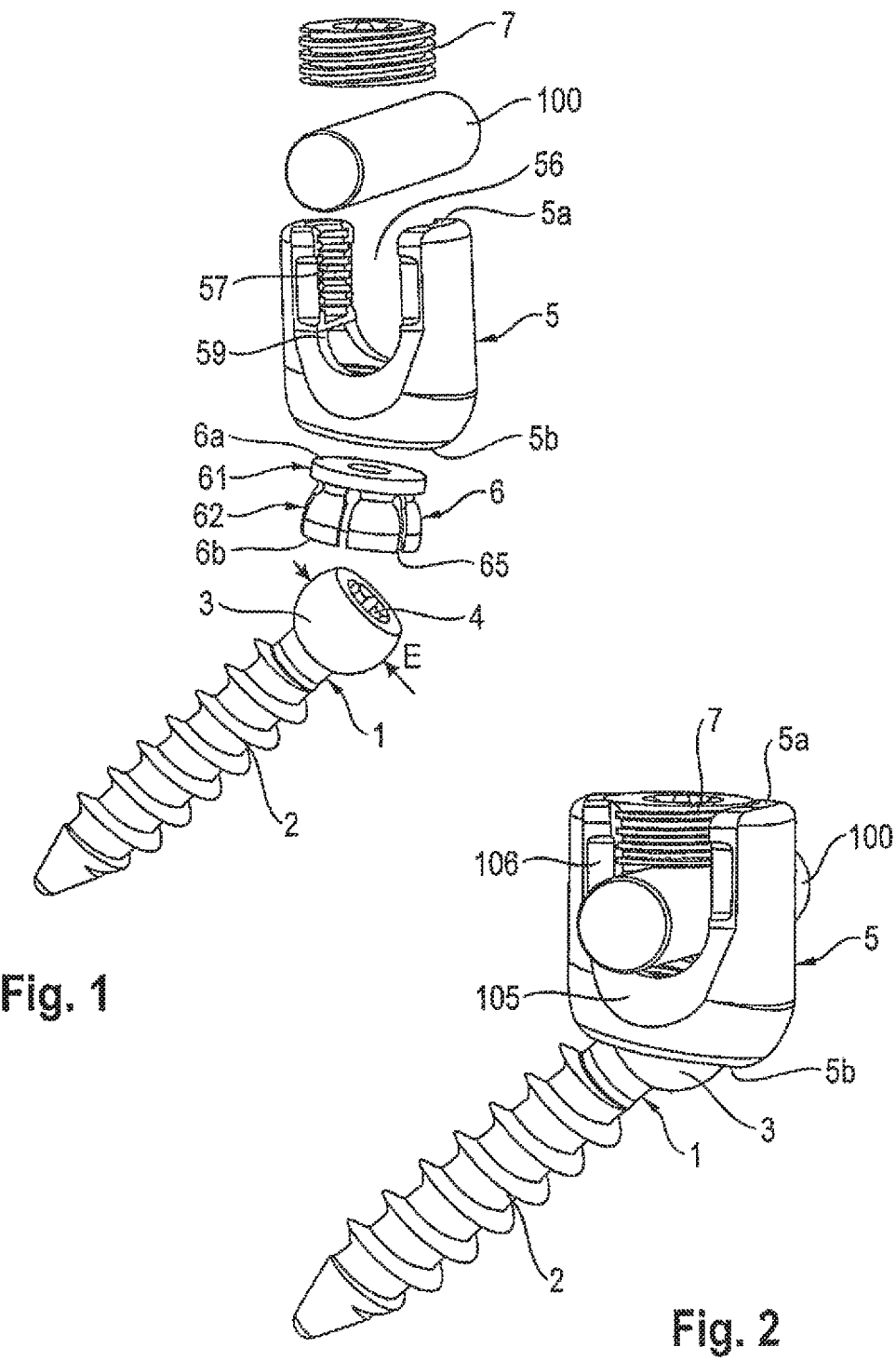
FIG. 1 shows an exploded perspective view of a polyaxial bone anchoring device according to a first embodiment.
FIG. 2 shows a perspective view of the polyaxial bone anchoring device of FIG. 1 in an assembled state.
Figure 3:
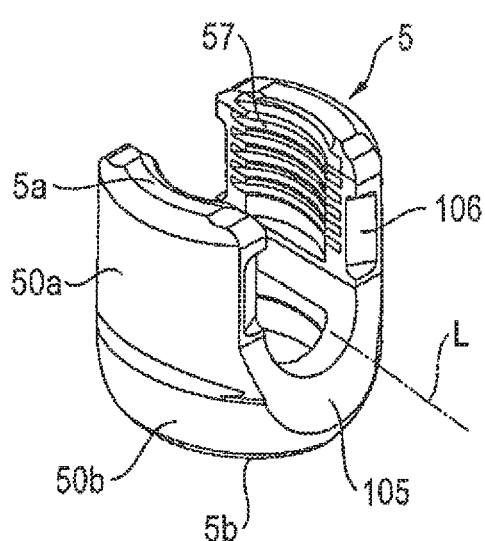
FIG. 3 shows a perspective view of the receiving part of the polyaxial bone anchoring device of FIG. 1.
Figure 4:
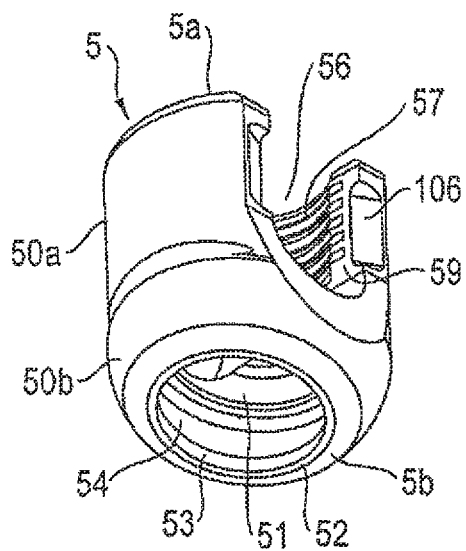
FIG. 4 shows another perspective view from the bottom of the receiving part of FIG. 3.
Figure 5:
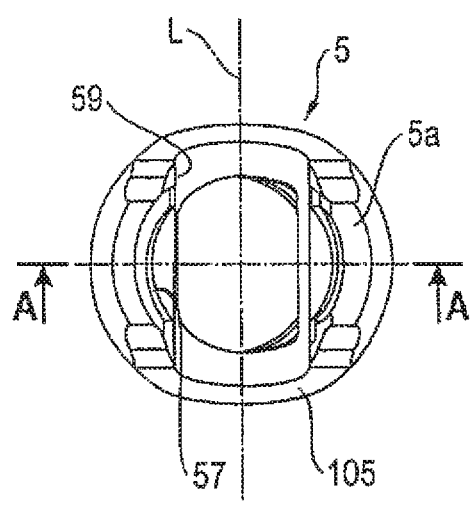
FIG. 5 shows a top view of the receiving part of FIG. 3.
Figure 6:
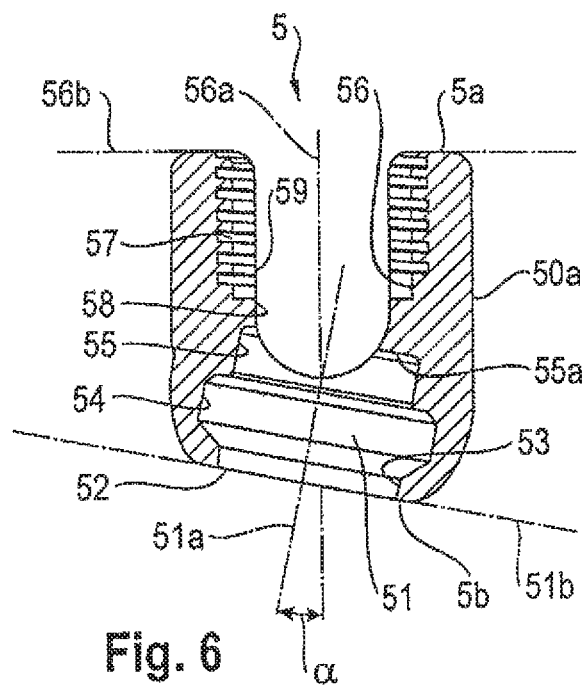
FIG. 6 shows a cross-sectional view of the receiving part along line A-A in FIG. 5.
Figure 7:
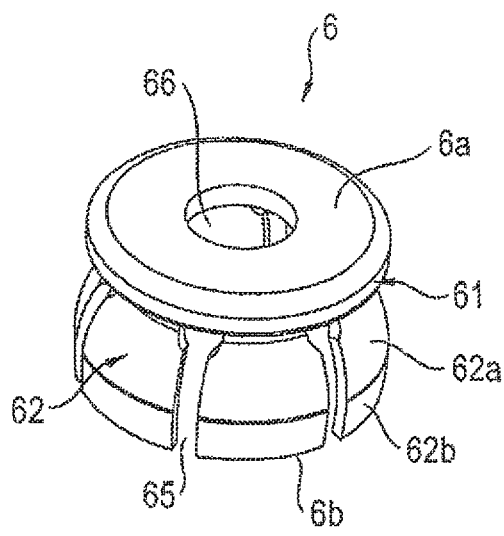
FIG. 7 shows a perspective view from the top of a compression member of the polyaxial bone anchoring device according to the first embodiment.
Figure 8:
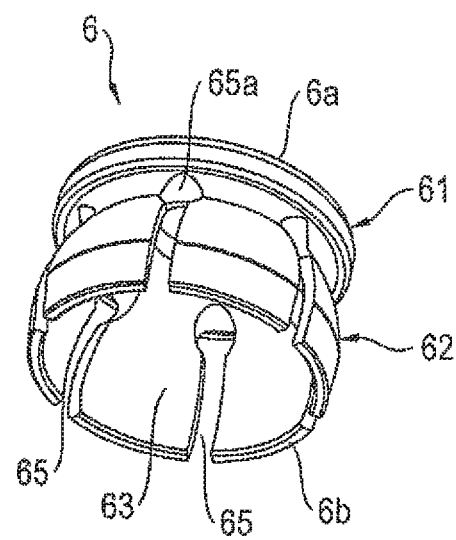
FIG. 8 shows another perspective view from the bottom of the compression member of FIG. 7.
Figure 9:
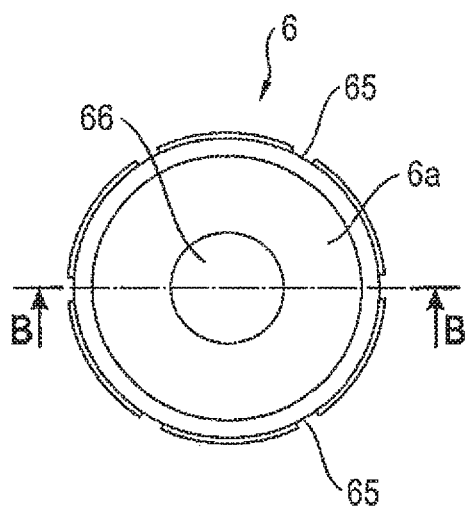
FIG. 9 shows a top view of the compression member of FIG. 7.
Figure 10:
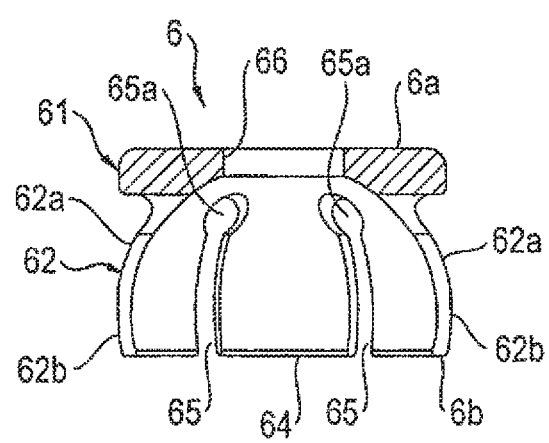
FIG. 10 shows a cross-sectional view of the compression member along line B-B in FIG. 9.

As shown in FIGS. 1 and 2, a polyaxial bone anchoring device according to a first embodiment includes a bone anchoring element 1 in the form of a bone screw having a threaded shank 2 and a spherical segment-shaped head 3. The head 3 has a recess 4 for engagement with a tool. The spherical segment-shaped head 3 may comprise a section including a largest diameter E of the head 3. The bone anchoring device further includes a receiving part 5 for receiving a rod 100 to connect the rod 100 to the bone anchoring element 1. In the receiving part 5, a compression member 6 for exerting pressure onto the head 3 is arranged. Furthermore, a locking element, in the form of, for example, an inner screw 7 is provided for securing and fixing the rod 100 and for locking the head 3 in the receiving part 5.

Referring further to FIGS. 3 to 6, the receiving part 5 has a top end 5a and a bottom end 5b. An outer surface of the receiving part is substantially cylindrical adjacent to the top end 5a and extends to a tapering surface portion 50b adjacent to the bottom end 5b. A first passage 51 that is coaxial with a first longitudinal axis 51a extends from the bottom end 5b toward the top end 5a. A second passage 56 coaxial with a second longitudinal axis 56a extends from the top end 5a toward the bottom end 5b. As can be seen in particular in FIGS. 5 and 6, the first passage 51 and the second passage 56 are in communication with one another. The first longitudinal axis 51a and the second longitudinal axis 56a include an angle α with one another and intersect at a point in the interior of the receiving part 5. By means of this design, the bottom end 5b defines a first plane 51b and the top end 5a defines a second plane 56b, wherein the first plane 51b and the second plane 56b intersect. The angle α included by the first longitudinal axis 51a and the second longitudinal axis 56a may be between around 5° and around 20°, for example, approximately 15°.

The passages are now described in more detail. The first passage 51 provides for an opening 52 at the bottom end 5b, wherein a diameter of the opening 52 is greater than the greatest diameter E of the head 3. Adjacent to the bottom end 5b the first passage 51 comprises a tapered section 53 that narrows toward the bottom end 5b. Following the tapered section 53 an enlarged section 54 is provided with an inner diameter that is greater than an inner diameter of the tapered section 53 and that provides a space so that the compression member 6 can expand therein. Following the enlarged section 54, there is a cylindrical section 55 with a smaller diameter compared to the enlarged section 54, the end of which provides for a stop 55a that limits an upward movement of the compression member 6.

The second passage 56 comprises adjacent to the top end 5a a section 57 with an internal thread that operates with the thread of the inner screw 7. Following the threaded section 57, there is a section 58 with a reduced inner diameter compared to the section 57 and the cylindrical section 55 of the first passage, thereby providing the stop 55a. Furthermore, adjacent to the top end 5a, a substantially U-shaped recess 59 is provided that extends into the direction of the bottom end 5b. By means of the U-shaped recess 59, a channel for receiving the rod 100 is provided. The channel axis L extends perpendicular to the second longitudinal axis 56*a*.

The receiving part 5 may further have inclined cuts 105 on either end of the channel formed by the U-shaped recess 59 that reduce the outer diameter of the receiving part 5 in a direction of the channel axis L. Furthermore, tool engagement recesses 106 may be provided on either end of the channel and on both sidewalls of the channel. The channel axis L and the second longitudinal axis 56*a* define a plane. The first longitudinal axis 51*a* extends at an angle relative to that plane, i.e. intersects the plane. Therefore, an asymmetry in view of the pivot angle of the bone anchoring element is provided transverse to the channel L, which is transverse to the rod axis.

Referring further to FIGS. 7 to 10, the compression member 6 has a top end 6*a* and a bottom end 6*b*. Adjacent to the top end 6*a*, there is a substantially cylindrical portion 61 with a flat surface at the top end 6*a* and with an outer diameter that is only slightly smaller than an inner diameter of the section 55 of the first passage 51 so that the cylindrical section 61 fits into the cylindrical section 55 of the passage and can move therein in axial direction of the first longitudinal axis 51*a*.

Following the cylindrical portion 61, the compression member 6 has a cap-like portion 62 that is recessed with respect to the cylindrical portion 61 at a position adjacent to the cylindrical portion 61. The cap-like portion 62 defines a hollow interior 63 forming a seat for the head 3 of the bone anchoring element 1. The hollow interior 63 is substantially spherically-shaped mating the spherical shape of the head 3. The second end 6*b* of the compression member has an opening 64 for the insertion of the head 3. An outer wall of the cap-like portion 62 comprises a first section 62*a* that is spherical and a second section 62*b* adjacent to the opening 64 that is tapered. The tapered section 62*b* of the compression member 6 cooperates with the tapered section 53 of the first passage 51 of the receiving part 5. The cap-like portion 62 of the compression member further comprises a plurality of slits 65 extending from an edge of the opening 64 through the cap-like portion up to a distance from the cylindrical portion 61. The respective ends 65*a* of the slits may have the shape of a section of a circle or may be otherwise enlarged with respect to the dimension of the slits 65 to facilitate a radial expansion or compression of the compression member. The dimension of the hollow interior 63, the number and dimensions of the slits 65 are such that the wall of the cap-like portion 62 is flexible enough to snap onto the head 3 when the head 3 is being inserted. The seat provided by the cap-like portion 62 of the compression member 6 allows pivoting of the head 3 in a symmetrical fashion relative to a central axis of the compression member 6.

A maximum outer diameter of the cap-like portion 62 can be slightly larger than the inner diameter of the lower opening 52 of the receiving part 5 at the bottom end 5*b*, because the cap-like section 62 can be compressed during insertion of the compression member 6 into the first passage 51 through the lower opening 52. A length in axial direction of the compression member 6 is such that when the compression member 6 is inserted into the first passage 51 of the receiving part 5 and when it abuts with the top end 6*a* against the stop 55*a* of the receiving part 5, the second end 6*b* is located above the tapered section 53 of the first passage 51 of the receiving part (FIGS. 13 and 14) to allow a radial expansion of the cap-like portion 62. Because the compression member 6 is symmetric with respect to the pivoting of the head 3, securing of the compression member 6 against rotation is not necessary.

The compression member 6 further comprises a coaxial bore 66 for providing access to the screw head 3 by a tool.

The inner screw 7 has a thread corresponding to the internal thread provided in the second passage 56. Preferably, a thread form that prevents the walls of the channel from splaying is used. Such a thread form can be, for example, a flat thread, a negative angle thread or a saw-tooth thread.

All parts described before may be made of a bio-compatible material, such as a bio-compatible metal like stainless steel or titanium, or a bio-compatible metal alloy, for example, Nitinol, or are made of a bio-compatible plastic material, for example, polyetheretherketone (PEEK). The parts may be of the same or of different materials.

The steps of assembling the bone anchoring device are now explained with respect to FIGS. 11 to 14. First, as shown in FIGS. 11 and 12, the compression member 6 is introduced from the bottom end 5*b* through the opening 52 into the first passage 51 of the receiving part 5. When the cap-like portion 62 of the compression member 6 passes the tapered section 53 of the first passage 57, it is slightly compressed. The compression member is further moved upward in the first passage 51 toward the first end 5*a* of the receiving part 5 until it abuts against the stop 55*a* of the cylindrical section 55. In this position, the bottom end 6*b* of the compression member 6 is above the tapered section 53 of the first passage 51 and is located in the enlarged section 54 that provides space for a radial expansion of the cap-like portion 62.

When the compression member 6 is in its uppermost position at the stop 55*a*, the head 3 of the bone anchoring element 1 is inserted into the first passage 51 of the receiving part 5 through the lower opening 52 at the bottom end 5*b*. When the head 3 enters into the hollow interior 63 through the lower opening 64 of the compression member 6, the cap-like portion 62 expands radially thereby permitting the insertion of the head 3, as shown in FIG. 13. When the head 3 has entered the hollow interior 63, the tapered outer surface section 62*b* of the cap-like portion 62 encompasses the head 3 at its greatest diameter E.

The use of the polyaxial bone anchoring device is now described with reference to FIGS. 15 and 16. The receiving part 5 may be delivered in a pre-assembled manner with the compression member 6 inserted into the first passage 51. After assembling the head 3 of the anchoring element 1 with the receiving part 5, the anchoring element 1 is inserted into a bone part or a vertebra. Typically, at least two bone anchoring devices are used that are connected with a rod 100. After insertion of the anchoring elements into the bone or into vertebrae, the receiving parts 5 are aligned to allow the insertion of the rod 100 by pivoting them with respect to the bone anchoring elements 1. The angular position may be held in a preliminary manner by friction between the head 3 and the cap-like portion 62, when the compression member 6 is moved downward so that its outer tapered section 62*b* engages the tapered section 53 of the first passage 51. After insertion of the rod 100, the inner screw 7 is inserted and tightened thereby moving the compression member 6 further downward so that it is compressed around the head 3 to lock the head 3 and the rod 100.

Figure 15:
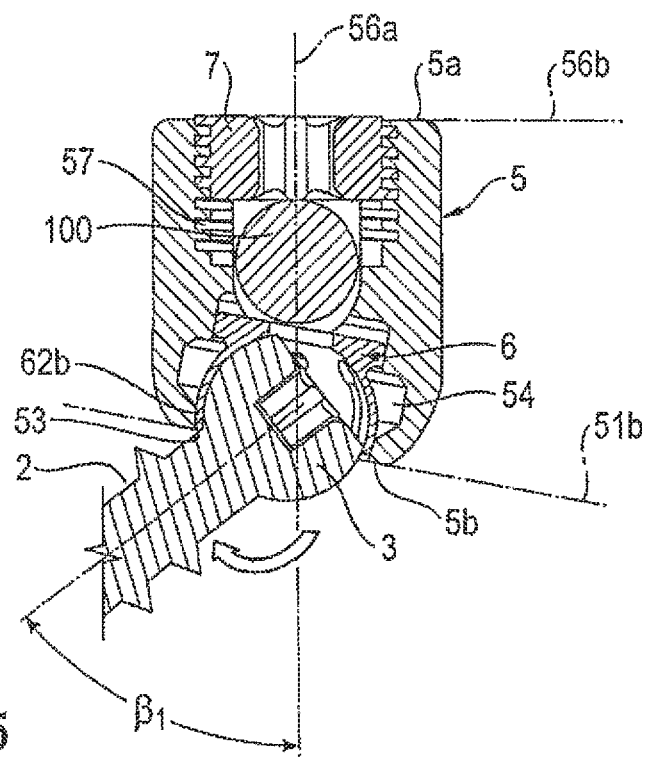
FIG. 15 shows a cross-sectional view of the polyaxial bone anchoring device in an assembled state, the section taken along line A-A of the receiving part shown in FIG. 5, wherein the bone anchoring element and the receiving part are pivoted relative to one another with a maximum pivot angle in a first direction.

As can be seen in FIG. 15, in the assembled state, there is a first maximum pivot angle $\beta_1$ relative to the second longitudinal axis 56*a*, which is defined by the abutment of the shank 2 of the bone anchoring element 1 against the lower end 5*b* of the receiving part in one direction.

Figure 16:
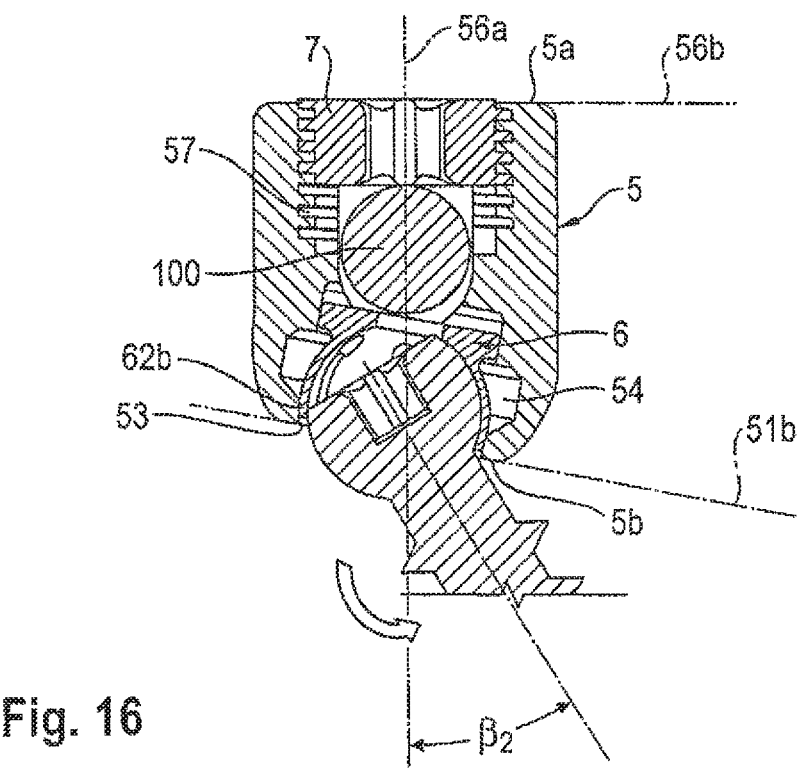
FIG. 16 shows a cross-sectional view of the polyaxial bone anchoring device in an assembled state, the section taken along line A-A of the receiving part shown in FIG. 5, wherein the bone anchoring element and the receiving part are pivoted relative to one another with a maximum pivot angle in a second direction opposite to the first direction.
Figure 17:
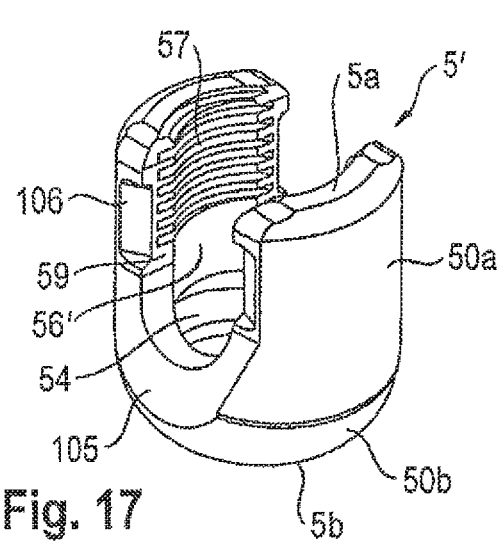
FIG. 17 shows a perspective view of a receiving part according to a modified first embodiment.
Figure 18:
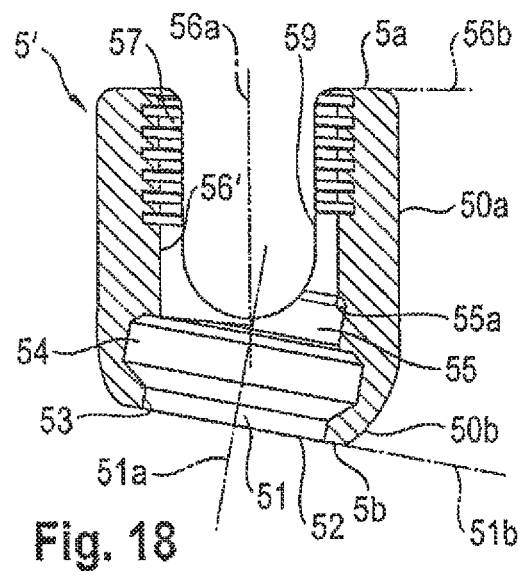
FIG. 18 shows a cross-sectional view of the receiving part of FIG. 17, the section taken in a plane perpendicular to the rod axis and going through the middle of a channel for the rod.

As can be seen in FIG. 16, a second maximum pivot angle β2 relative to the second longitudinal axis 56*a* is defined by the abutment of the shank 2 against the lower end 5*b* in an opposite direction. The first maximum pivot angle $β_1$ is greater than the second maximum pivot angle β2. While the pivoting of the bone anchoring element 1 relative to the receiving part 5 is symmetrical relative to the first longitudinal axis 51*a*, the pivoting is asymmetrical relative to the second longitudinal axis 56*a*, and is therefore also asymmetrical relative to the channel axis L and the rod 100.

Because the seat for the head 3 provided by the compression member 6 is symmetrical with respect to the pivoting of the head 3, the pull-out force for the head 3 is not decreased compared to comparable polyaxial bone anchoring devices without an enlarged pivot angle.

The polyaxial anchoring device may be particularly useful in applications of cervical spine surgery, wherein enlarged pivot angles only to one side and to an opposite side may be needed.

A modification of the first embodiment of the polyaxial bone anchoring device is shown in FIGS. 17 to 21. The modified first embodiment differs in the shape of the receiving part and is identical or highly similar to the first embodiment in all other parts. The receiving part 5' has a second passage 56' with a diameter greater than the outer diameter of the cylindrical portion 61 of the compression member 6. The second passage 56' extends into the cylindrical section 55 of the first passage 51. Therefore, as can be seen in particular in FIGS. 18 and 19, the inner diameter of the second passage 56' is sized such as to allow the introduction of the compression member 6 from the top end 5*a*.

Figure 19:
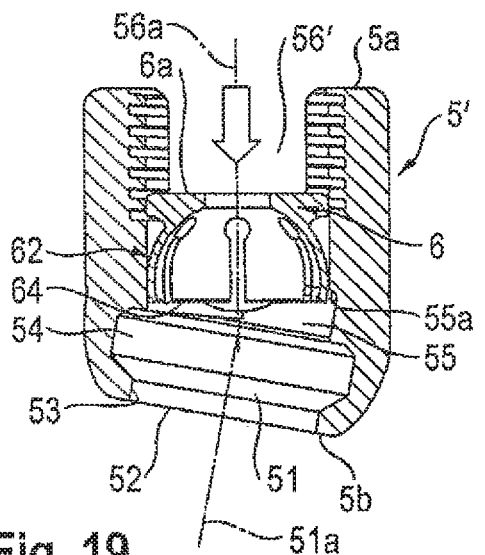
FIGS. 19 to 21 show cross-sectional views of steps of mounting the compression member to the receiving part according to the modified first embodiment.
Figure 20:
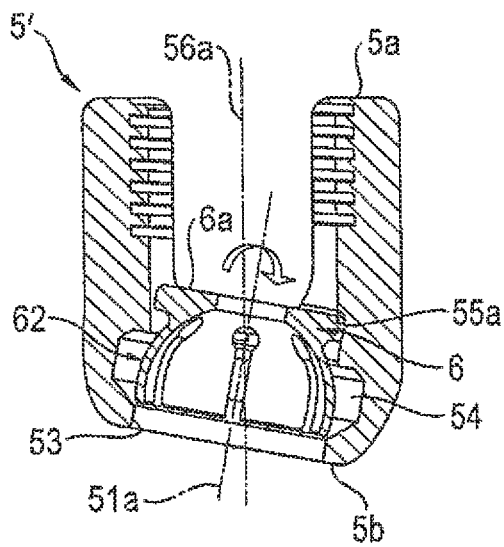
Figure 21:
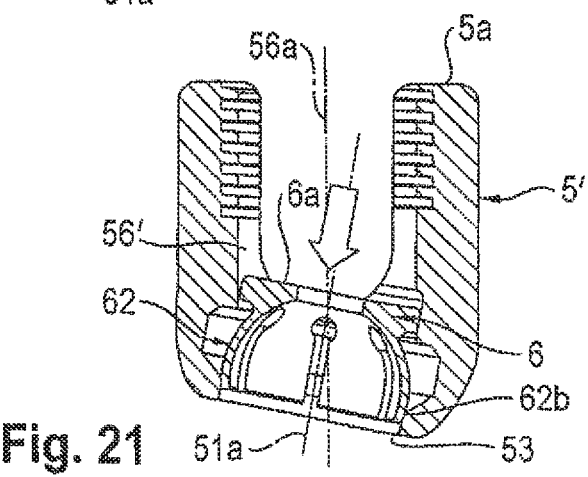

Steps of assembling the receiving part 5' and the inner compression member 6 are shown in FIGS. 19 to 21. As depicted in FIG. 19, the compression member 6 is introduced into the first passage 56' in an orientation in which the opening 64 shows toward the bottom end 5*b* of the receiving part 5'. When the compression member 6 has reached the cylindrical section 55 of the first passage 51, the compression member 6 is tilted to align it with the first longitudinal axis 51*a* so that it can engage the cylindrical section 55 of the first passage 51 as can be seen in FIG. 20. As shown in FIG. 21, the compression member 6 can further be moved downward until its tapered outer section 62*b* engages the tapered section 53 of the receiving part 5'. The other steps are the same as for the first embodiment.

In a still further modified embodiment, a transverse pin (not shown) can be provided in the receiving part that cooperates with the compression member to secure the compression member against tilting once it has reached its position in the first passage.

Alternatively, with the modified first embodiment, the compression member 6 can also be inserted from the bottom end 5*b* of the receiving part 5'.

A second embodiment the polyaxial bone anchoring device is now described with reference to FIGS. 22 to 38. As shown in particular in FIGS. 22 and 23, a polyaxial bone anchoring device according to the second embodiment differs from the polyaxial bone anchoring device according to the first embodiment in that instead of an inner compression member, an outer locking ring 8 is used that is configured to compress a portion of a receiving part 500 to clamp and lock the head 3 therein. All portions of the second embodiment that are identical with the function or the design of corresponding portions of the first embodiment have the same reference numerals and the description thereof will not be repeated.

The receiving part 500 comprises a first portion 9 that is adjacent to the bottom end 5*b* and a second portion 10 that is adjacent to the top end 5*a*. The first portion 9 comprises the first passage 51 coaxial with the first longitudinal axis 51*a* and the second portion 10 comprises the second passage 56 coaxial with the second longitudinal axis 56*a*. As in the first embodiment, the first and the second longitudinal axes intersect and include an angle α. The plane 51*b* defined by the bottom end 5*b* is inclined relative to the plane 56*b* defined by the top end 5*a* and therefore, the planes intersect.

At the bottom end 5*b*, the first portion 9 has an opening 91 the diameter of which is such that the head 3 can be inserted. At a distance from the bottom end 5*b*, the first passage 51 comprises a head receiving portion 92 having a spherical segment shape that mates the shape of a portion of the head 3. The head receiving portion 92 provides a seat for the head 3 that allows the head 3 to pivot therein. Furthermore, the head receiving portion 92 is configured to encompass the head 3 of the bone anchoring element 1 laterally, thereby covering the largest diameter E of the head 3.

A plurality of slits 93 are provided in the head receiving portion 92 that are open to the second end 5*b*. The slits 93 render the head receiving portion 92 flexible so that it can be expanded when the head 3 is inserted and can be compressed to clamp and finally lock the head 3 by means of friction. The number and size of the slits 93 is provided depending on the desired flexibility of the head receiving portion 92.

Figure 27:
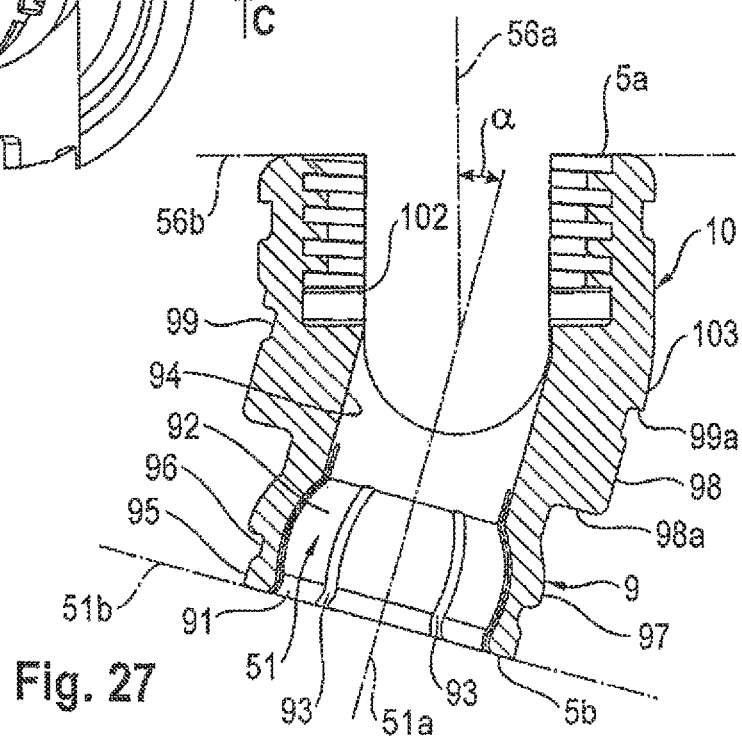
FIG. 27 shows a cross-sectional view of the receiving part according to the second embodiment along line C-C in FIG. 26.
Figure 28:
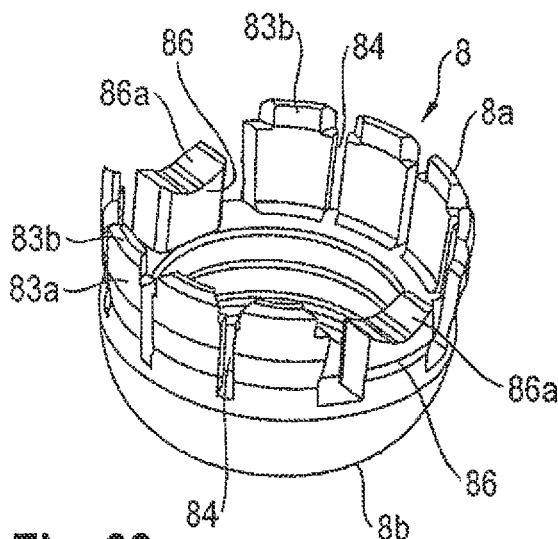
FIG. 28 shows a perspective view of a locking ring of the polyaxial bone anchoring device according to the second embodiment.
Figure 29:
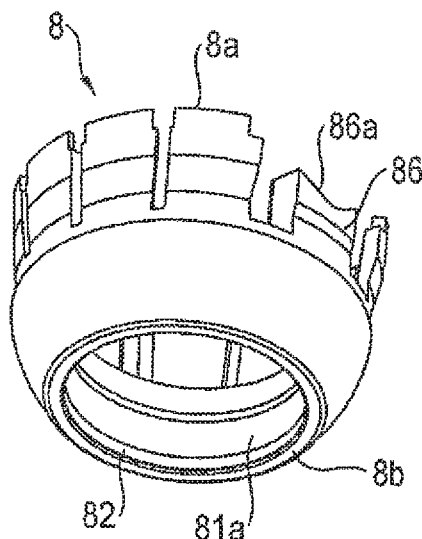
FIG. 29 shows another perspective view from the bottom of the locking ring of FIG. 28.
Figure 30:
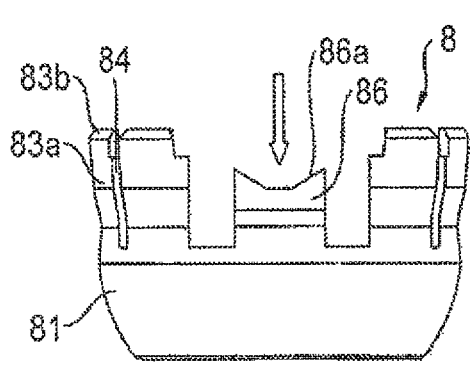
FIG. 30 shows a side view of the locking ring of FIG. 28.
Figure 31:
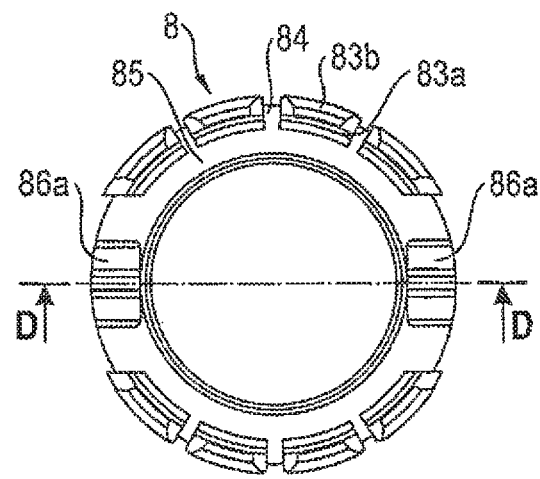
FIG. 31 shows a top view of the locking ring of FIG. 28.
Figure 32:
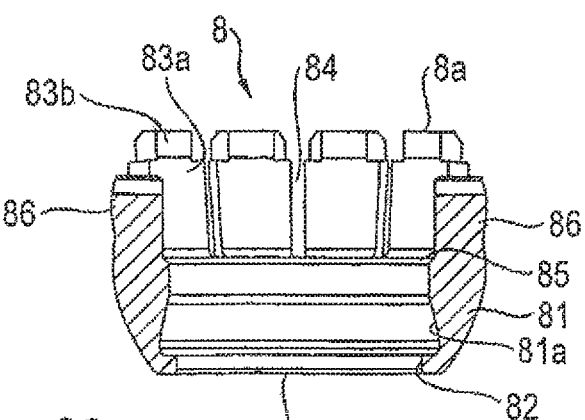
FIG. 32 shows a cross-sectional view of the locking ring along line D-D in FIG. 31.

As can be seen in particular in FIG. 27, the head receiving portion is rotationally symmetrical with respect to the first longitudinal axis 51*a*. More in detail, when the head 3 is inserted into the head receiving portion 92, it can pivot to a maximum pivot angle in one direction and to the same maximum pivot angle in the opposite direction in relation to the first longitudinal axis 51*a*.

Following the head receiving portion 92, the first passage 51 further comprises a cylindrical section 94 extending to a distance from the bottom end 5*b*. At least some of the slits 93 may extend into the cylindrical section 94 to increase the flexibility of the head receiving portion 92.

The outer surface of the first portion 9 of the receiving part 500 comprises several sections. Adjacent to the bottom end 5*b* there is a cylindrical section 95. Following the cylindrical section 95 there is a circumferentially extending lower groove 96. Adjacent to the lower groove 96 there is an outwardly curved or conically widening section 97, the diameter of which increases toward the bottom end 5*b*. Adjacent to or at some distance from the outwardly curved section 97 there is a cylindrical section 98 that is symmetrical in relation to the first longitudinal axis 51*a*. An outer diameter of the cylindrical section 98 is greater than an outer diameter of the outwardly curved section 97. A downward facing surface of the cylindrical section 98 forms a stop 98*a* for the locking ring 8. Adjacent to the cylindrical section 98, a circumferentially extending upper groove 99 is provided for engagement with a portion of the locking ring 8. The upper groove 99 has an upper wall providing a stop 99*a* for the locking ring 8.

The second portion 10 of the receiving part 500 comprises the second passage 56 that consists of a internally threaded section 101 adjacent to the top end 5*a*. Furthermore, the second portion 10 comprises a substantially U-shaped recess 102 extending from the top end 5*a* toward the bottom end 5*b* into the first passage 51. Hence, the bottom of the U-shaped recess 102 reaches into the hollow cylindrical section 94 of the first passage 51.

Figure 24:
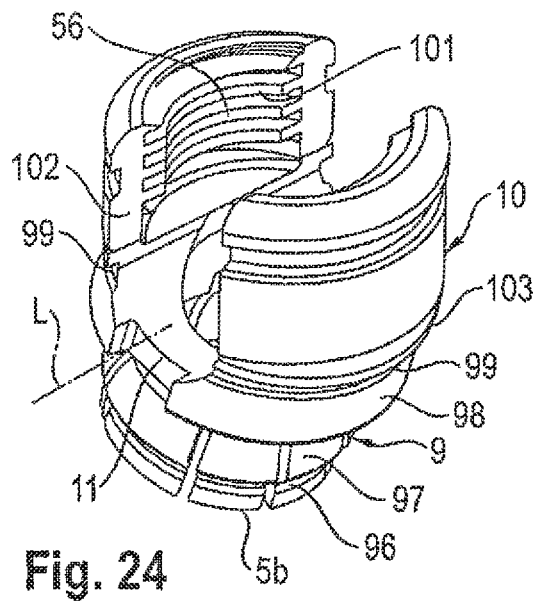
FIG. 24 shows a perspective view of the receiving part of the polyaxial bone anchoring device according to the second embodiment.
Figure 25:
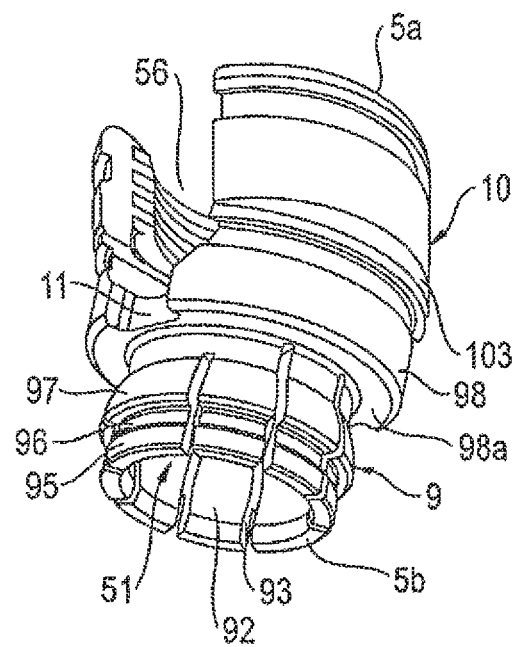
FIG. 25 shows another perspective view from the bottom of the receiving part according to the second embodiment.
Figure 26:
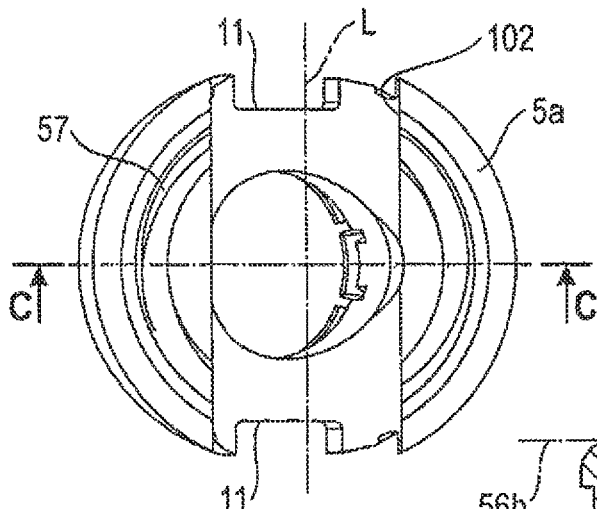
FIG. 26 shows a top view of the receiving part according to the second embodiment.

An outer surface of the second portion 10 is substantially cylindrical and may continue in a small tapered section 103 at the transition between the second portion 10 and the first portion 9. Further, as can be seen in FIGS. 24 to 26 cut-outs 11 are provided in the cylindrical section 98 of the first portion 9 on either end of the channel formed by the U-shaped recess 102.

The locking ring 8 is now described referring to FIGS. 28 to 32. The locking ring 8 has an upper end 8a and a lower end 8b. In the mounted state, the upper end 8a is oriented in the direction of the top end 5a of receiving part 500, while the lower end 8b is oriented toward the bottom end 5b of the receiving part 500. Near the lower end 8b, a first portion 81 with an inner surface 81a is provided that cooperates with the outwardly curved section 97 of the receiving part 500 to compress the head receiving portion 92. The outer surface of the first portion 81 may also be tapered to reduce an outer bottom diameter. The size of the first portion 81 is such that, for example, the tapered inner surface 81a can engage the outwardly curved section 97 of the head receiving portion 92 to exert a compression force onto the head receiving portion 92. The inner surface 81a of the first portion 81 of the locking ring 8 can also be curved with a curvature directed toward a center of the locking ring 8.

At the lower end 8b, the locking ring 8 includes an inwardly projecting edge 82, an inner diameter of which is smaller than an inner diameter of the other portions of the locking ring 8. The inwardly projecting edge 82 is configured to engage the lower groove 96 of the receiving part 500.

The locking ring 8 further has upwardly extending wall portions 83a that are separated from each other by slits 84. The upwardly extending wall portions 83a are arranged at an outer circumference of an inner circumferential shoulder 85 of the locking ring 8, and render the upper portion of the locking ring flexible. The number and size of the slits and the thickness of the wall portions 83a are configured such that a desired flexibility is realized. At the free ends of the wall portions 83a engagement sections 83b are provided that are shaped so as to engage the upper groove 99 provided on the outer surface of the receiving part 500.

The locking ring 8 is sized in such a way with respect to the first portion 9 of the receiving part 500, that the head receiving portion 92 can expand within the locking ring 8 to allow the insertion of the head 3 when the locking ring 8 is in the first position as shown in FIG. 34.

Two projections 86 that are located diametrically opposite to each other, are formed between the flexible wall portions 83a of the locking ring 8. The projections 86 have a height where they extend into the cut-outs 11 and project above the bottom of the U-shaped recess 102, when the locking ring 8 is in a position in which the head 3 is not yet locked as shown in FIGS. 34 and 35. A free end surface 86a of the projections 86 is concave. For example, the free end surface 86a can be substantially V-shaped to provide two lines of contact with the rod 100.

The locking ring 8 is arranged in such a manner around the first portion 9 of the receiving part 500 that the projections 86 are located at positions of (e.g., are aligned with) the U-shaped recess 102. In this case, the projections 86 prevent the locking ring 8 from rotating when the rod 100 is not inserted.

The flexibility of the head receiving portion 92 and the size of the head receiving portion allows for assembling the locking ring 8 from the bottom end 5b onto the first portion 9.

Steps of assembling the polyaxial bone anchoring device are described with reference to FIGS. 33 to 36. In a first step, shown in FIG. 33, the locking ring 8 is mounted onto the first portion 9 of the receiving part 500 from the bottom end 5b with its flexible wall portions 83a oriented toward the top end 5a. When mounting the locking ring 8, the head receiving portion 92 is slightly compressed. As shown in FIG. 34, the locking ring 8 is moved upward until its circumferential shoulder 85 abuts against the lower surface 98a of the cylindrical outer surface section 98 of the first portion 9. The flexible wall portions 83a are not in engagement with the upper groove 99. The projections 86 extend into the cut-outs 11 and project over the bottom of the U-shaped recess 102. The locking ring 8 is held in a preliminary manner in this position because the inwardly projecting edge 82 engages the lower groove 96.

As shown in FIG. 35, the head 3 of the bone anchoring element 1 can be inserted into the head receiving portion 92 of the first portion 9 when the locking ring 8 is in the position descibed before.

In a next step (not shown), the locking ring 8 may be moved downward toward the bottom end 5b until its flexible wall portions 83a resiliently snap into the upper groove 99. Once in this position, the free upper edge of the engagement portions 83b abut against the stop 99a of the groove 99, thereby preventing upward movement of the locking ring 8 out of this position. In this configuration, the head 3 is prevented from removal through the lower opening 91. Furthermore, in this configuration, the head 3 may be clamped by friction so that a certain angular position may be maintained in a preliminary manner.

In a next step, as shown in FIG. 36, the rod 100 is inserted into the channel from the top end 5a until it abuts against the free surface 86a of the projections 86. Because the first and second longitudinal axes are tilted with respect to one another, the engagement of the rod 100 with the free end surface 86a is slightly asymmetric. If the free end surface 86a provides for a contact along two lines, for example with a V-shaped cross-section, a safe contact can be achieved even in such asymmetric engagement condition.

Once the inner screw 7 is inserted into the receiving part 500 and tightened, the force exerted by the rod 100 onto the projections 86 of the locking ring 8 move the locking ring 8 downward into a final position in which the head receiving portion 92 is compressed so as to lock the head 3.

Figure 37:
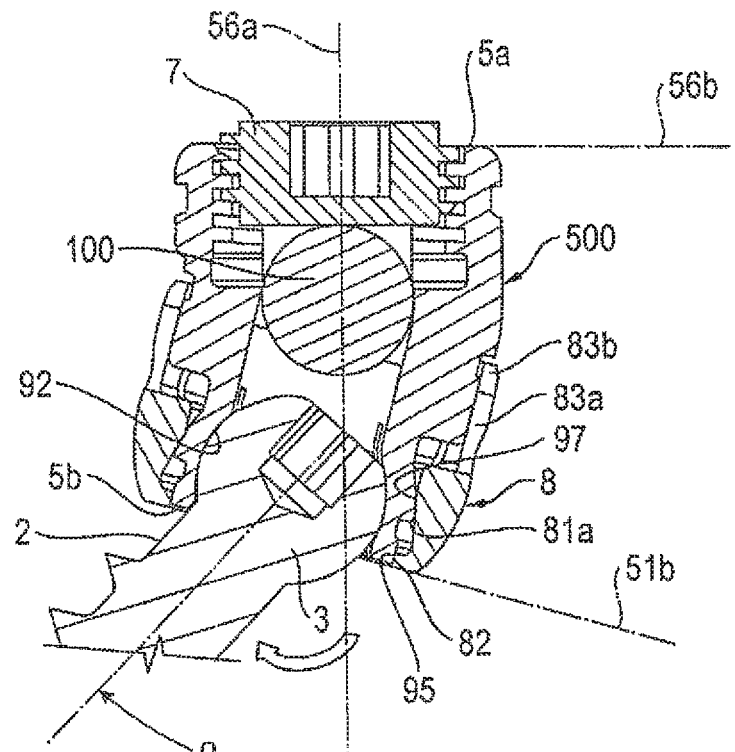
FIG. 37 shows a cross-sectional view of the polyaxial bone anchoring device according to the second embodiment in an assembled state, wherein the bone anchoring element and the receiving part are pivoted relative to one another with a maximum pivot angle in a first direction.
Figure 38:
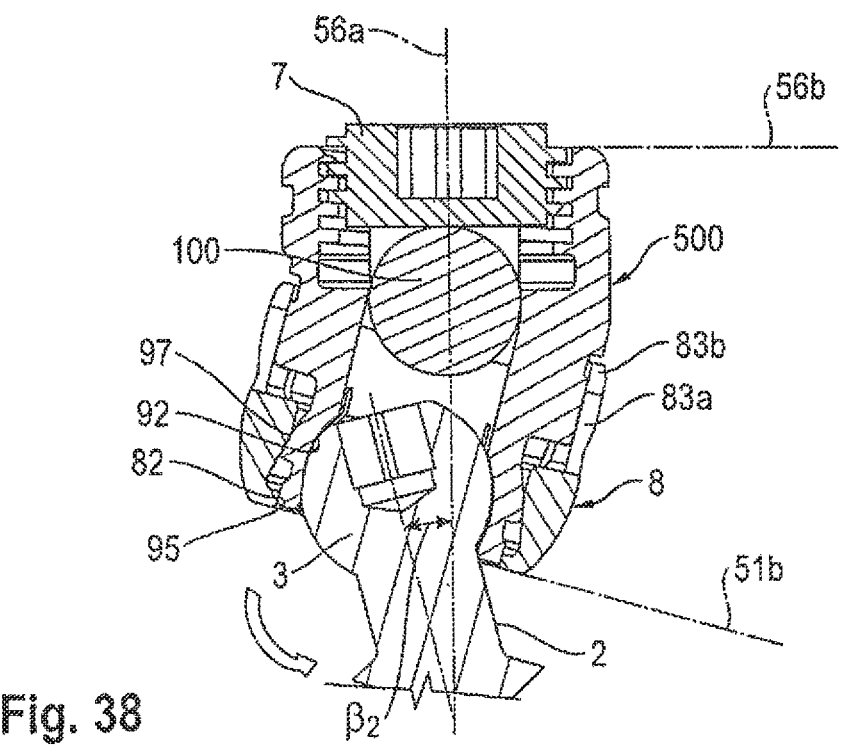
FIG. 38 shows a cross-sectional view of the polyaxial bone anchoring device according to the second embodiment in an assembled state, wherein the bone anchoring element and the receiving part are pivoted relative to one another with a maximum pivot angle in a second direction opposite to the first direction.

FIGS. 37 and 38 show an assembled configuration, wherein the bone anchoring element 1 is pivoted relative to the receiving part 500 at a maximum pivot angle $\beta_1$ to one side (FIG. 37) and a maximum pivot angle (32 to the opposite side (FIG. 38). The maximum pivot angle is defined by the abutment of the shank 2 against the lower portion of the seat. The maximum pivot angle $\beta_1$ in FIG. 37 is larger than the maximum pivot angle (32 in FIG. 38 because of the inclination of the first passage 51 of the receiving part 500 with respect to the second passage 56.

Modifications of this embodiment are possible. The locking ring can have any other shape that fulfills the function of compressing the head receiving portion. The surface of the free end of the projections can be flat. Alternatively, the projections can be omitted as long as the rod can engage the locking ring to move it downward. The outer surface of the first portion and the inner surface of the locking ring can have other shapes that allow for compression of the first portion by means of an increasing force when the locking ring is shifted downward relative to the receiving part.

For both embodiments, the orientation of the first longitudinal axis relative to the second longitudinal axis may be different from the orientation described before. For example, the first longitudinal axis may lie in the plane defined by the channel axis and the second longitudinal axis. The resulting pivoting of the bone anchoring element is then asymmetric in a direction along the rod axis. The first longitudinal axis may also be angled at an acute angle with respect to said plane and with respect to the channel axis.

Furthermore, the seat may be substantially symmetrical with respect to the pivoting of the head when the head pivots in any direction and the opposite direction thereof. Small cutouts at the lower edge of the seat may be present. In addition, the head and the seat may be configured to allow a symmetric pivoting in one or more discrete planes only so that the bone anchoring device has a monoplanar construction with respect to the pivot angles.

Modifications of both embodiments may further include the use of specific materials for rendering the compression member or the head receiving portion flexible. Such materials can be used instead of or additionally to providing slits.

For the bone anchoring element, various different kinds of anchoring elements can be used and combined with the receiving part. These anchoring elements may be, for example, screws with different length, screws with different diameters, cannulated screws, screws with different thread forms, nails, hooks etc. For some anchoring elements, the head and the shaft may also be separate parts that are connectable to each other.

Other kinds of locking devices including outer nuts, outer caps, bayonet locking devices, or others are also possible. Also, a two part locking device may be used wherein one part locks the head and the other part locks the rod.

It shall also be noted that portions of the different described embodiments can also be combined with each other in various different combinations.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A receiving part for coupling a rod to a bone anchoring element, the receiving part comprising:
   a top end, a bottom end, and a longitudinal axis that extends from the top end toward the bottom end;
   two arms defining a channel open to the top end for receiving the rod, wherein the channel extends perpendicularly to the longitudinal axis through opposing sides of the receiving part, and wherein a width of the channel at the first end is substantially the same for both of the opposing sides of the receiving part;
   an opening at the bottom end for the bone anchoring element, wherein the longitudinal axis extends through the opening; and
   an inner surface in which an internal groove having a bottom is formed, wherein the internal groove extends circumferentially around a central axis that is oriented at an angle oblique to the longitudinal axis.

2. The receiving part of claim 1, wherein the internal groove is substantially symmetrical with respect to the central axis.

3. The receiving part of claim 1, wherein a first passage extends coaxially with the central axis from the bottom end toward the top end, and a second passage extends coaxially with the longitudinal axis from the top end toward the bottom end.

4. The receiving part of claim 1, wherein the channel is formed by a substantially U-shaped recess extending from the top end.

5. The receiving part of claim 1, further comprising a locking element configured to be advanced along the longitudinal axis into the channel for locking the position of the receiving part relative to the bone anchoring element.

6. The receiving part of claim 5, wherein the locking element is configured to urge an inserted rod toward the bottom end of the receiving part, which clamps a head of the bone anchoring element in the receiving part to lock the receiving part and the bone anchoring element from further movement relative to one another.

7. The receiving part of claim 1, wherein the opening at the bottom end of the receiving part has a diameter that is greater than a greatest diameter of a head of the bone anchoring element, such that the head is insertable into the receiving part from the bottom end.

8. The receiving part of claim 1, wherein the receiving part is configured to allow pivoting of the bone anchoring element in a symmetrical manner relative to the central axis.

9. A polyaxial bone anchoring device comprising the receiving part of claim 1 and an inner member positionable at least partially in the internal groove, the inner member defining a seat for a head of the bone anchoring element.

10. The polyaxial bone anchoring device of claim 9, wherein the inner member has at least one slit to facilitate expansion and/or compression.

11. The polyaxial bone anchoring device of claim 9, wherein the inner member is configured to cover at least a portion of the head from an upper side of the head.

12. The polyaxial bone anchoring device of claim 9, wherein the inner member is movable in the internal groove, and wherein movement of the inner member toward the top end of the receiving part is restricted by a stop.

13. The polyaxial bone anchoring device of claim 9, wherein the internal groove provides space to facilitate expansion of the inner member when the head is inserted therein.

14. The polyaxial bone anchoring device of claim 9, wherein the inner member has a spherically-shaped outer wall.

15. The polyaxial bone anchoring device of claim 9, wherein the inner member has a spherically-shaped hollow interior forming the seat for the head.

16. The polyaxial bone anchoring device of claim 9, wherein the inner member has a diameter that is smaller than a diameter of the head.

17. A receiving part for coupling a rod to a bone anchoring element, the receiving part comprising:
   a top end, a bottom end, and a longitudinal axis that extends from the top end toward the bottom end;
   two arms at the top end defining a channel for receiving the rod;
   an opening at the bottom end for the bone anchoring element, wherein the longitudinal axis extends through the opening; and
   an inner surface in which an internal groove having a bottom is formed, wherein the internal groove extends circumferentially around a central axis that is oriented at an angle oblique to the longitudinal axis, with a side of the internal groove that extends closer axially to the top end oriented radially toward one of the two arms, and with an opposite side of the internal groove that extends closer axially to the bottom end oriented radially toward the other one of the two arms.

18. The receiving part of claim 17, wherein an axial distance between the top end of the receiving part and at least part of a downward facing surface at the bottom end that is oriented radially toward the one of the two arms is less than an axial distance between the top end and another part of the downward facing surface that is oriented radially away from the one of the two arms.

19. A polyaxial bone anchoring device comprising the receiving part of claim 17 and an inner member positionable at least partially in the internal groove, the inner member defining a seat for a head of the bone anchoring element.

20. A receiving part for coupling a rod to a bone anchoring element, the receiving part comprising:
- a top end, a bottom end, and a longitudinal axis that extends from the top end toward the bottom end;
- two arms at the top end defining a channel for receiving the rod;
- an opening at the bottom end for the bone anchoring element, wherein the longitudinal axis extends through the opening; and
- an inner surface in which an internal groove having a bottom is formed, wherein the internal groove extends circumferentially around a central axis that is oriented at an angle oblique to the longitudinal axis, with a side of the internal groove that extends closer axially to the top end oriented in a first radial direction toward one of the two arms;
- wherein an axial distance between the top end of the receiving part and at least part of a downward facing surface at the bottom end that is oriented in the first radial direction is less than an axial distance between the top end and another part of the downward facing surface that is oriented away from the first radial direction.

21. A polyaxial bone anchoring device comprising the receiving part of claim 20 and an inner member positionable at least partially in the internal groove, the inner member defining a seat for a head of the bone anchoring element, wherein when the inner member is positioned at least partially in the internal groove, the central axis defines an axis of rotation of the inner member.

22. The polyaxial bone anchoring device of claim 19, wherein when the inner member is positioned at least partially in the internal groove, the central axis defines an axis of rotation of the inner member.

23. The polyaxial bone anchoring device of claim 9, wherein when the inner member is positioned at least partially in the internal groove, the central axis defines an axis of rotation of the inner member.

24. The receiving part of claim 1, wherein the internal groove has at least an annular region forming an endless ring that is oriented at the angle oblique to the longitudinal axis.

* * * * *

UNITED STATES PATENT AND TRADEMARK OFFICE
CERTIFICATE OF CORRECTION

PATENT NO. : 11,154,334 B2
APPLICATION NO. : 16/924897
DATED : October 26, 2021
INVENTOR(S) : Lutz Biedermann et al.

It is certified that error appears in the above-identified patent and that said Letters Patent is hereby corrected as shown below:

In the Specification

Column 7, Line 4    Delete "(32" and insert -- $\beta_2$ --.

Column 7, Line 7    Delete "(32" and insert -- $\beta_2$ --.

Column 10, Line 53    Delete "(32" and insert -- $\beta_2$ --.

Column 10, Line 57    Delete "(32" and insert -- $\beta_2$ --.

Signed and Sealed this
Twentieth Day of December, 2022

Katherine Kelly Vidal
*Director of the United States Patent and Trademark Office*